United States Patent
MacMurray

(12) 
(10) Patent No.: US 8,109,409 B1
(45) Date of Patent: Feb. 7, 2012

(54) GARBAGE CAN DEODORIZER

(76) Inventor: Carolyn MacMurray, Portland, OR (US)

(*) Notice: Subject to any disclaimer, the term of this patent is extended or adjusted under 35 U.S.C. 154(b) by 148 days.

(21) Appl. No.: 12/356,378

(22) Filed: Jan. 20, 2009

(51) Int. Cl.
*B65D 1/42* (2006.01)
*B65D 6/34* (2006.01)
*B65D 8/08* (2006.01)
*A24F 25/00* (2006.01)
*A61L 9/04* (2006.01)

(52) U.S. Cl. .................. 220/651; 220/495.01; 220/645; 248/910; 239/54; 239/60

(58) Field of Classification Search .............. 239/34–60; 220/495.01–495.11
See application file for complete search history.

(56) References Cited

U.S. PATENT DOCUMENTS

| | | | |
|---|---|---|---|
| 2,067,547 A * | 1/1937 | Schneider et al. | 220/87.1 |
| 2,798,636 A | 7/1957 | Ketchledge | |
| 2,802,590 A * | 8/1957 | Tupper | 220/522 |
| 3,702,677 A | 11/1972 | Heffington | |
| 3,955,706 A | 5/1976 | Whitaker | |
| 4,268,392 A * | 5/1981 | Hayes | 210/238 |
| 4,349,104 A * | 9/1982 | Hayes | 206/205 |
| 4,813,791 A | 3/1989 | Cullen | |
| 5,046,604 A | 9/1991 | Forhetz | |
| 5,174,462 A | 12/1992 | Hames | |
| 5,390,818 A * | 2/1995 | LaBuda | 220/676 |
| 5,804,174 A | 9/1998 | Ishibashi | |
| 5,997,178 A | 12/1999 | Nye | |
| 6,814,249 B2 * | 11/2004 | Lin | 220/87.1 |
| 6,910,412 B2 * | 6/2005 | Ko | 100/229 A |
| 7,735,258 B2 * | 6/2010 | Vickery | 43/131 |
| 2003/0226773 A1 * | 12/2003 | Shaffer | 206/204 |
| 2007/0095839 A1 * | 5/2007 | Stone | 220/495.06 |
| 2008/0179329 A1 * | 7/2008 | Brooks et al. | 220/495.06 |
| 2010/0200592 A1 * | 8/2010 | Murdock et al. | 220/495.06 |

FOREIGN PATENT DOCUMENTS
WO 2004/103329 A1 12/2004
* cited by examiner

Primary Examiner — Len Tran
Assistant Examiner — James Hogan
(74) Attorney, Agent, or Firm — Christensen O'Connor Johnson Kindness PLLC

(57) ABSTRACT

The present application is directed to a deodorizer that comprises a package comprised of a porous compostable material and a crushable compostable material within the package that releases a deodorant when crushed. The application further describes a deodorizer assembly comprising an attachment assembly for removably attaching a deodorizer to the interior of a garbage container. The application also discloses a deodorizer assembly comprising a garbage can liner and a crushable compostable material that releases a deodorant when crushed.

6 Claims, 4 Drawing Sheets

GARBAGE CAN DEODORIZER

BACKGROUND

Separating compostable and biodegradable materials from non-compostable and non-biodegradable waste is increasingly desirable as land fill space becomes less available and disposal fees become more expensive. Many municipalities now require or are considering requiring residents to separate compostable and biodegradable materials from other forms of waste. The compostable and biodegradable materials are often stored in cans or other containers for one to several weeks before pickup. As a consequence, the decomposition of biomaterials inside the container often emits unpleasant or noxious odors into the surrounding environment. These unpleasant odors may be a nuisance to residents, particularly in urban areas where multiple containers containing decomposing biomaterials may be located in close proximity. The noxious odors that result from storing compostable biomaterials in curbside cans may decrease the compliance of residents to separate compostable biomaterials from non-compostable materials.

SUMMARY

The present application discloses a deodorizer comprised of a package made from a compostable material that is porous to allow gas flow from the interior of the package to the exterior of the package, and a crushable compostable material that is contained within the package, the crushable compostable material releasing a deodorant when crushed.

The present application also discloses a garbage container assembly comprised of a garbage container and a deodorizer, as described above. The application further describes a deodorizer assembly comprised of a garbage container liner and a deodorizer comprised of a crushable compostable material that releases a deodorant when crushed.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of the present disclosure will become more readily appreciated by reference to the following detailed description, when taken in conjunction with the accompanying drawings, wherein.

DETAILED DESCRIPTION

Figure 1:
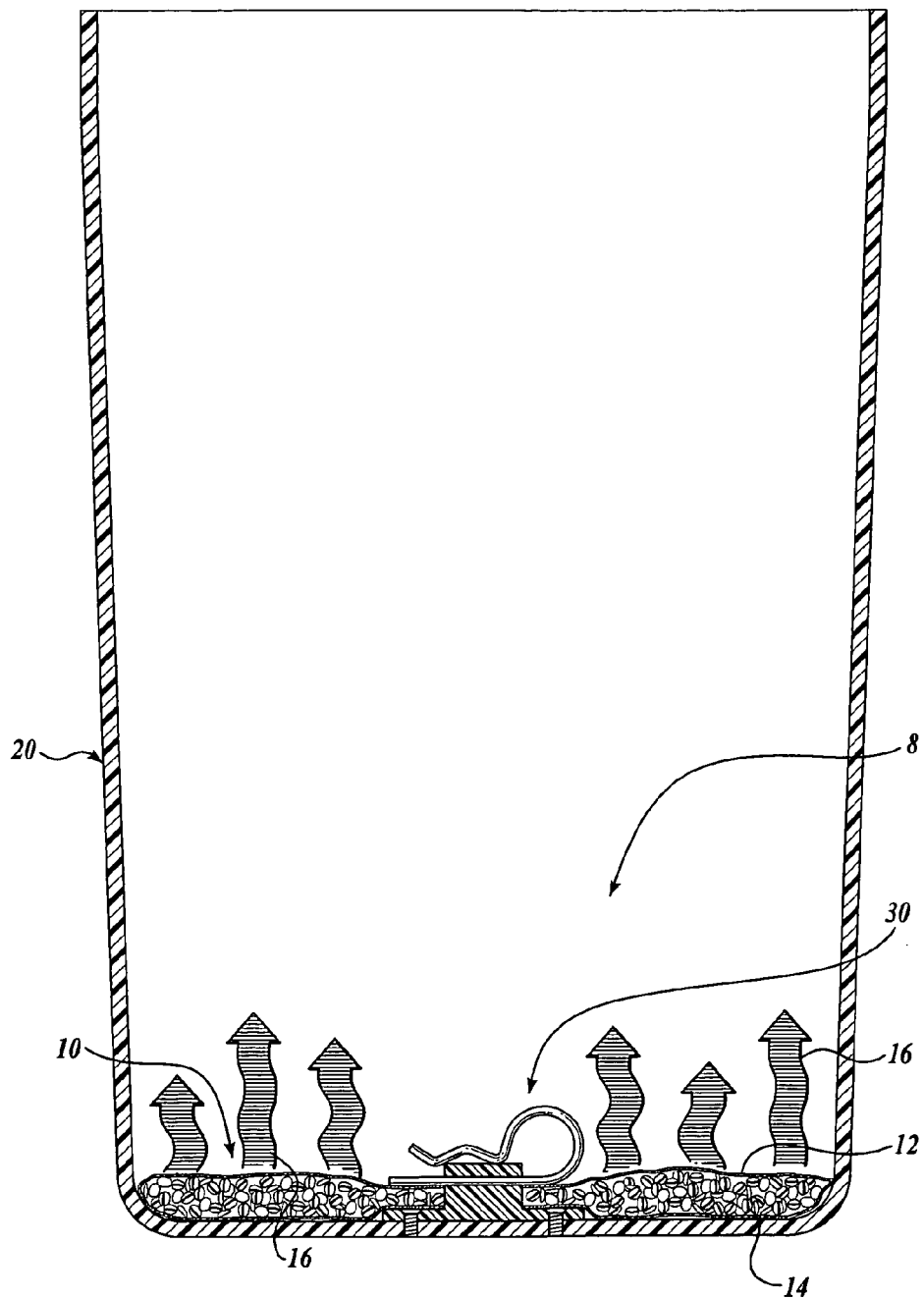
FIG. 1 is a cross-sectional view of a deodorizer assembly according to one embodiment of the present disclosure, wherein the deodorizer is removably secured to the bottom of a garbage container with an attachment assembly.

A deodorizer assembly 8 according to one embodiment of the present disclosure is best seen by referring to FIG. 1. The deodorizer assembly 8 includes a deodorizer 10 that is securable within an interior bottom portion of a garbage container 20 with a suitable attachment assembly 30. It will be understood that the term garbage container may refer to any appropriate container or receptacle that is suitable for holding garbage waste, compostable waste, or compostable biomaterials, including but not limited to containers designed for interior household use, curbside cans, recycling cans, dumpsters, and equivalents thereof of any of the foregoing containers. The deodorizer assembly may also be used within a garbage container having an interior liner, such as a garbage bag. Moreover, it should be appreciated that the deodorizer 10 may instead be used in any suitable container, storage device, or space in which deodorizing is desired.

The deodorizer 10 is comprised of a package 12 having an interior portion or compartment and an exterior portion and a crushable compostable material 14 disposed within the interior portion of the package 12. The package 12 is preferably made of a compostable material. Examples of suitable compostable materials include, but are not limited to, paper, various types of fabrics, particularly fabrics made from natural fibers such as cotton, flax, and hemp, and biodegradable materials, such as bioplastics and other materials capable of undergoing biological composition in a compost site. The package 12 is also preferably made of a substantially porous material that allows the flow of gas from the interior portion of the package to the exterior. Examples of substantially porous materials include, but are not limited to, paper, fabrics, or any other material having small holes or a loose mesh-like structure suitable for retaining the crushable compostable material 14 within the package while allowing gas exchange to occur between the interior and exterior of the package.

The crushable compostable material 14 disposed within the interior of the package 12 is any suitable material that releases a deodorant when crushed. A preferred crushable compostable material 14 is coffee beans. Some of the coffee beans may be precrushed to release the deodorant aroma 16 of coffee before adding garbage to the container. In other embodiments, the deodorizer 10 may comprise another natural or artificial compostable material that releases a deodorant when crushed, such as charcoal. In the alternative, the crushable material may be a container filled with a solid or liquid deodorant that releases the deodorant when crushed.

Referring still to FIG. 1, a representative attachment assembly 30 for removably attaching the deodorizer 10 to the bottom of the garbage container 20 will be hereinafter described. The attachment assembly 30 may be any suitable device that removably secures the deodorizer 10 to a suitable interior portion or surface of a garbage container 20 or other storage device. It is preferred that the deodorizer be secured to the bottom interior surface of a garbage container 20 such that the crushable compostable material 14 disposed within the interior of the package 12 is crushed by garbage as it is deposited into the garbage container 20.

Figure 2:
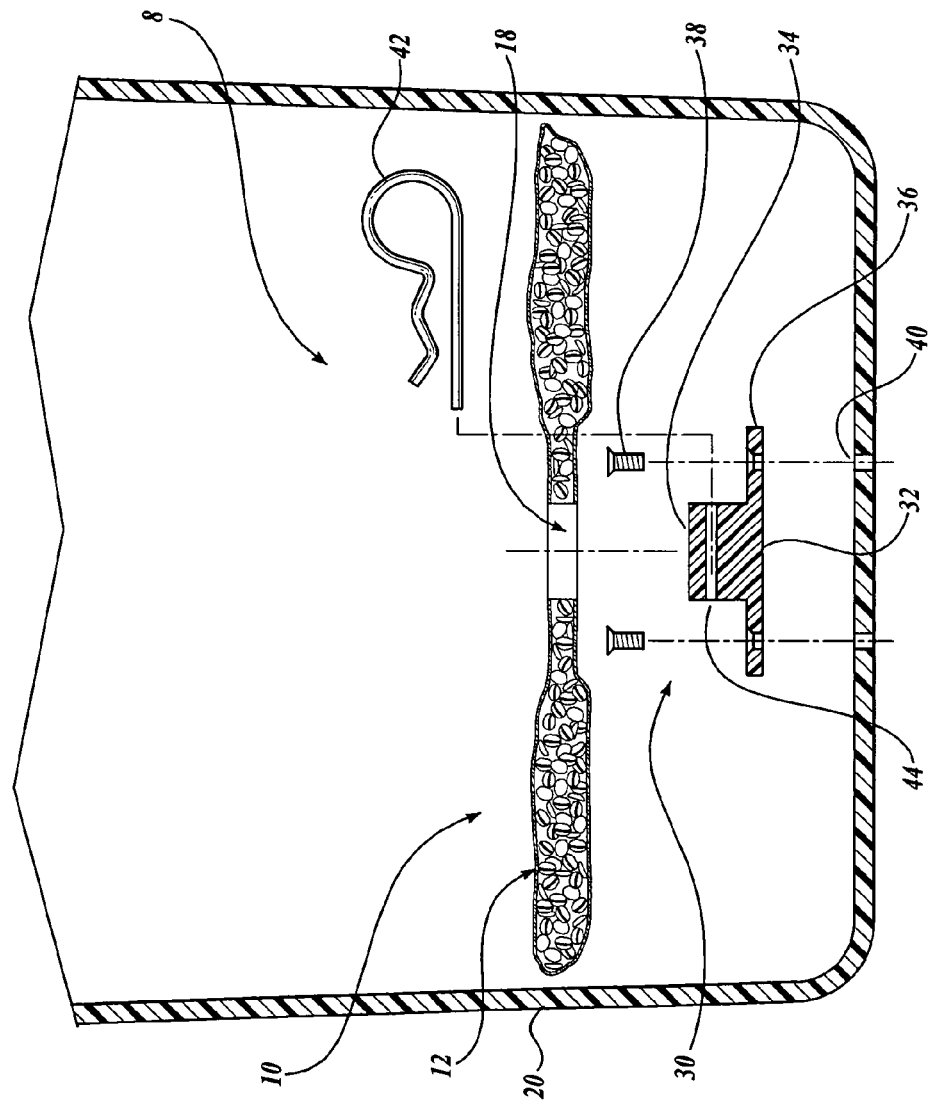
FIG. 2 is a cross-sectional exploded view of the deodorizer and attachment assembly of FIG. 1.

Referring to FIG. 2, the attachment assembly 30 preferably includes a basal member 32 having a central post 34 extending upwardly from a flange portion 36. The basal member is configured to be secured within the bottom of a garbage container 20 with any suitable fastening means such that the flange portion 36 abuts the bottom interior surface of the garbage container 20 and the central post 34 extends upwardly therefrom. Those of skill in the art will appreciate that any suitable fastening means may be used, including but not limited to fasteners 38 such as screws, bolts, rivets, or an adhesive. For instance, fasteners 38 may pass through openings in the flange portion 36 and be thereafter received into corresponding threaded openings 40 formed in the bottom of the garbage container 20.

The deodorizer package 12 has a centrally located hole 18 that is sized and configured to receive the central post 34 therein. The package 12 is secured on the central post 34 by any suitable manner. In one example illustrated in FIG. 2, a pin 42 is receivable within a transverse through-hole 44 formed in the central post 34 of the basal member 32. The transverse through-hole 44 is formed in a predetermined location on the central post 34 such that the pin 42 is positioned just above the deodorizer 10 when the deodorizer is positioned in the bottom of the garbage container 20. The pin 42 may also be positioned to contact the deodorizer 10 so as to provide downward pressure to prevent the deodorizer 10 from moving. Moreover, it is preferred that the pin 42 is of a suitable length such that the pin 42 engages a suitable portion of the deodorizer 10 to secure it against the bottom of the garbage container 20. The pin 42 may be any suitable pin, such as a cotter pin.

In an alternative embodiment (not shown), the central post 34 of the basal member 32 could be threaded, and the retaining means may comprise a threaded retaining member that, in operation, screws down over the central post 34, wherein the threaded member has a wide flange at the upper end that presses down on a portion of the deodorizer 10 to secure it against the bottom of the garbage container 20. Examples of other suitable retaining means for removably attaching the deodorizer 10 to the basal member 32 include, but are not limited to, clips, threaded couplings, friction couplings, and equivalents thereof.

The attachment assembly 30 may be included in a kit suitable for retrofitting an existing garbage container 20. For instance, the kit may include the basal member 32, fasteners 38, and pin 42 or other retaining means as described above. In one embodiment, the kit includes the necessary tools for mounting the basal member 32 to the inside of a garbage container 20. In another embodiment, the kit provides written instructions for mounting the basal member 32 to the interior of the garbage container 20 and for securing the deodorizer 10 to the basal member 32 with the pin 42. If other embodiments of the attachment assembly 30 are used, the kit may include suitable instructions for mounting a portion of the attachment assembly 30 to the garbage container 20 and for securing the deodorizer 10 to the interior of the garbage container 20 with the attachment assembly 30. In other embodiments, the attachment assembly 30 may be provided with the garbage container 20 as an integral component of the garbage container 20. For example, the attachment assembly could be injection molded into the bottom of a plastic garbage container.

Referring to FIGS. 1 and 2, the manner in which the deodorizer assembly 8 is used will be hereinafter described. Unless the attachment assembly 30 is previously integrated into the garbage container 20, the basal member 32 of the attachment assembly 30 is first mounted to the bottom interior surface of the garbage container 20 with the fasteners 38 or other suitable fastening means. Thereafter, the deodorizer 10 is removably attached to the bottom of the garbage container 20 by fitting the deodorizer 10 onto the central post 34 of the basal member 32 and thereafter passing the pin 42 through the through-hole 44 in the central post 34.

With the deodorizer 10 received within the garbage container 20, the crushable compostable material 14 inside the package 12 is crushed by the weight of the garbage that is added to the garbage container 20. As the compostable material 14 is crushed by the weight of the garbage, the crushable compostable material 14 releases a deodorant aroma 16 that passes from the interior portion of the package 12 to the exterior portion of the package 12 to deodorize the garbage container 20. When more garbage is added to the garbage container 20, progressively more of the coffee beans are crushed by the weight of the added garbage, resulting in the release of additional deodorant aromas. As a result, the deodorant aroma released from the deodorizer 10 substantially corresponds to the amount of garbage received within the garbage container 20, thereby offsetting the odor caused by the garbage. It will be understood that the term garbage includes food waste, compostable waste, compostable biomaterials, recyclable biomaterials, or any other material that generates odors during decomposition.

When the garbage container 20 is emptied, the attachment assembly 30 retains the deodorizer 10 inside the interior of the garbage container 20, allowing the deodorizer 10 to be reused multiple times. When the user determines that the deodorizer 10 is no longer effective or after the deodorizer 10 has been used a predetermined number of times, the pin 42 may be removed from within the through-hole 44 to release the deodorizer 10 from the basal member 32. The deodorizer 10 may thereafter be replaced with a new deodorizer, if so desired.

Figure 3:
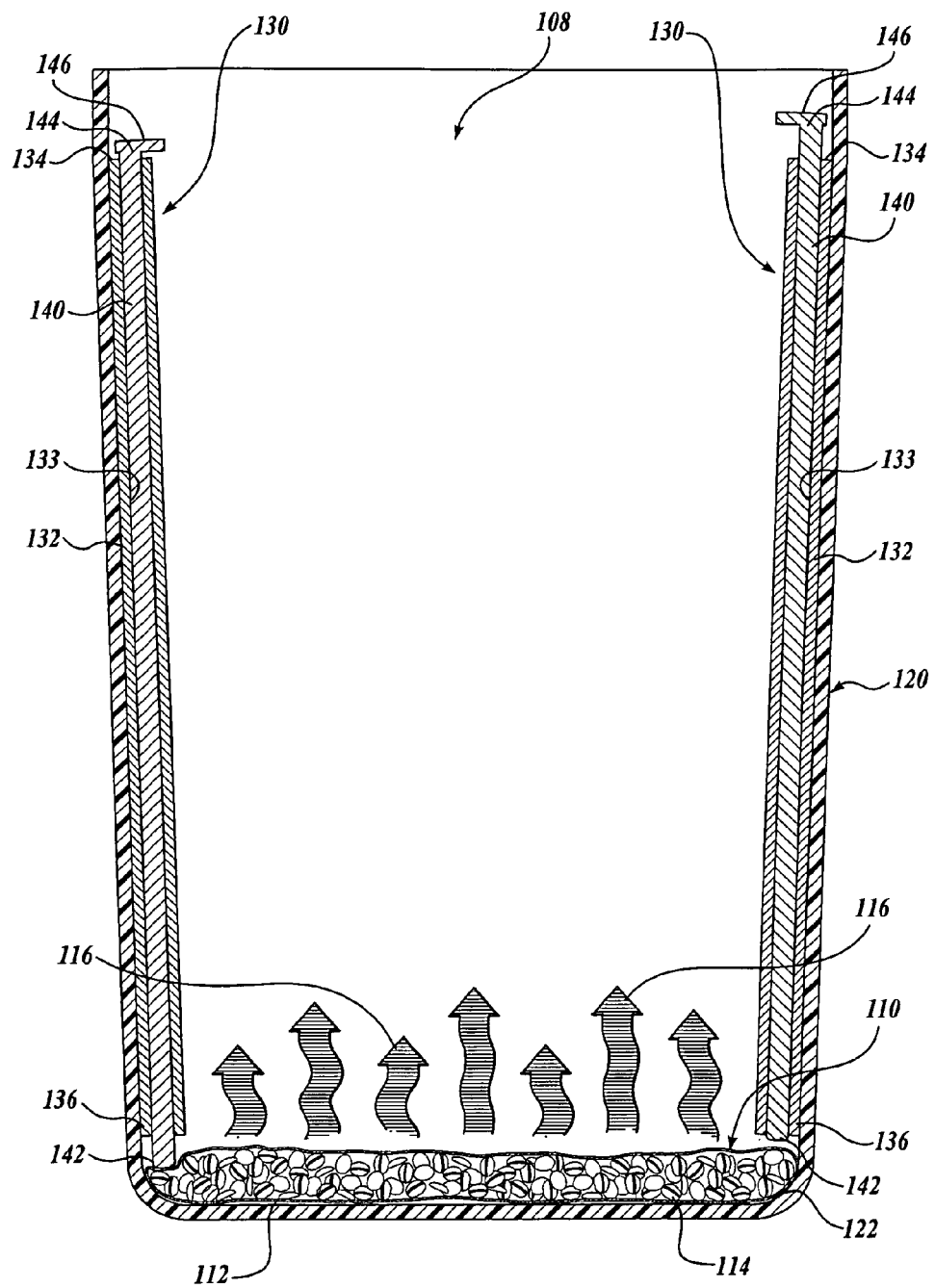
FIG. 3 is a cross-sectional view of a first alternate embodiment of the deodorizer and attachment assembly in accordance with the present disclosure.

Referring to FIG. 3, a first alternate embodiment of a deodorizer assembly 108 will be hereinafter described. The deodorizer assembly 108 includes an attachment assembly 130 for retaining a deodorizer 110 inside a garbage container 120. The deodorizer 110 is substantially identical to the deodorizer 10 described above except that the deodorizer 110 does not include a centrally located hole 18 formed in the package 112. The attachment assembly 130 includes one or more channel-defining structures 132 formed on or otherwise secured to the interior side walls of a garbage container 120. It is preferred, but not required, that at least two channel-defining structures 132 be used.

The channel-defining structures 132 are preferably substantially vertical, and each includes an interior channel 133, a top end 134 defining a top opening and a bottom end 136 defining a bottom opening. The top ends 134 are located near the opening of the garbage container 120. The bottom ends 136 are located in the vicinity of the interior bottom portion 122 of the garbage container 120 to define a sufficient gap to receive the deodorizer 110 between the bottom ends 136 of the channel-defining structures 132 and the interior bottom portion 122 of the garbage container 120.

An elongated member 140 is configured to be slideably disposed within each of the channels 133 of the channel-defining structures 132. The channels 133 and elongated members 140 may be square, rectangular, ovoid, round or any other suitable cross-sectional shape such that the elongated members 140 are slidably receivable within the channels 133. The elongated members 140 preferably have a length that is greater than the length of the channel-defining structures 132. In this manner, a first end 142 of the elongated members 140 contacts the deodorizer package 112 disposed between the bottom ends 136 of the channel-defining structures 132 and the interior bottom portion 122 of the garbage container 120 to secure the deodorizer 110 within the bottom interior portion 122 of the garbage container 120. A second end 144 of the elongated members 140 extends above the top end 134 of the channel-defining structures 132. The second end 144 may define a flanged portion or enlarged end portion 146 to provide a handle for pulling the elongated members 140 out from within the channel-defining structures 132 for disassembly of the attachment assembly 130.

Referring to FIG. 3, the manner in which the attachment assembly 130 is used will be hereinafter described. The deodorizer 110 is placed inside the garbage container 120 at the interior bottom portion 122 thereof such that the crushable compostable material 114 releases deodorant aromas 116, when, for instance, the deodorizer 110 is crushed by garbage. The elongated members 140 are inserted within the channels 133 of the channel-defining structures 132. The first ends 142 of the elongated members 140 contact the deodorizer package 112, thereby pressing the deodorizer 110 against the interior bottom portion 122 of the garbage container 120. Thus, when the garbage container 120 is inverted, for example, when emptied, the elongated members 140 retain the deodorizer 110 against the interior bottom portion 122 of the garbage container 120. The elongated members 140 may be configured so as to be frictionally received within the channel 133 so as to prevent movement of the elongated member 140 when the garbage container 120 is inverted. When the user determines that the deodorizer 110 is no longer effective or after the deodorizer 110 has been used a predetermined number of times, the elongated members 140 are partially or completely removed from the channel-defining structures 132 to release the deodorizer 110 from the interior bottom portion 122 of the garbage container 120. The deodorizer 110 may thereafter be replaced with a new deodorizer, if so desired.

In an alternative embodiment (not shown), the elongated members 140 may be releasably attachable to the channel-defining structures 132 at a predetermined position within the channel-defining structures 132 by any suitable releasable attachment mechanism. Examples of suitable releasable attachment mechanisms include fasteners such as pins or clips. Preferably, the releasable attachment mechanism would be located near the top end 134 of the channel-defining structures 132 for easy access.

Figure 4:
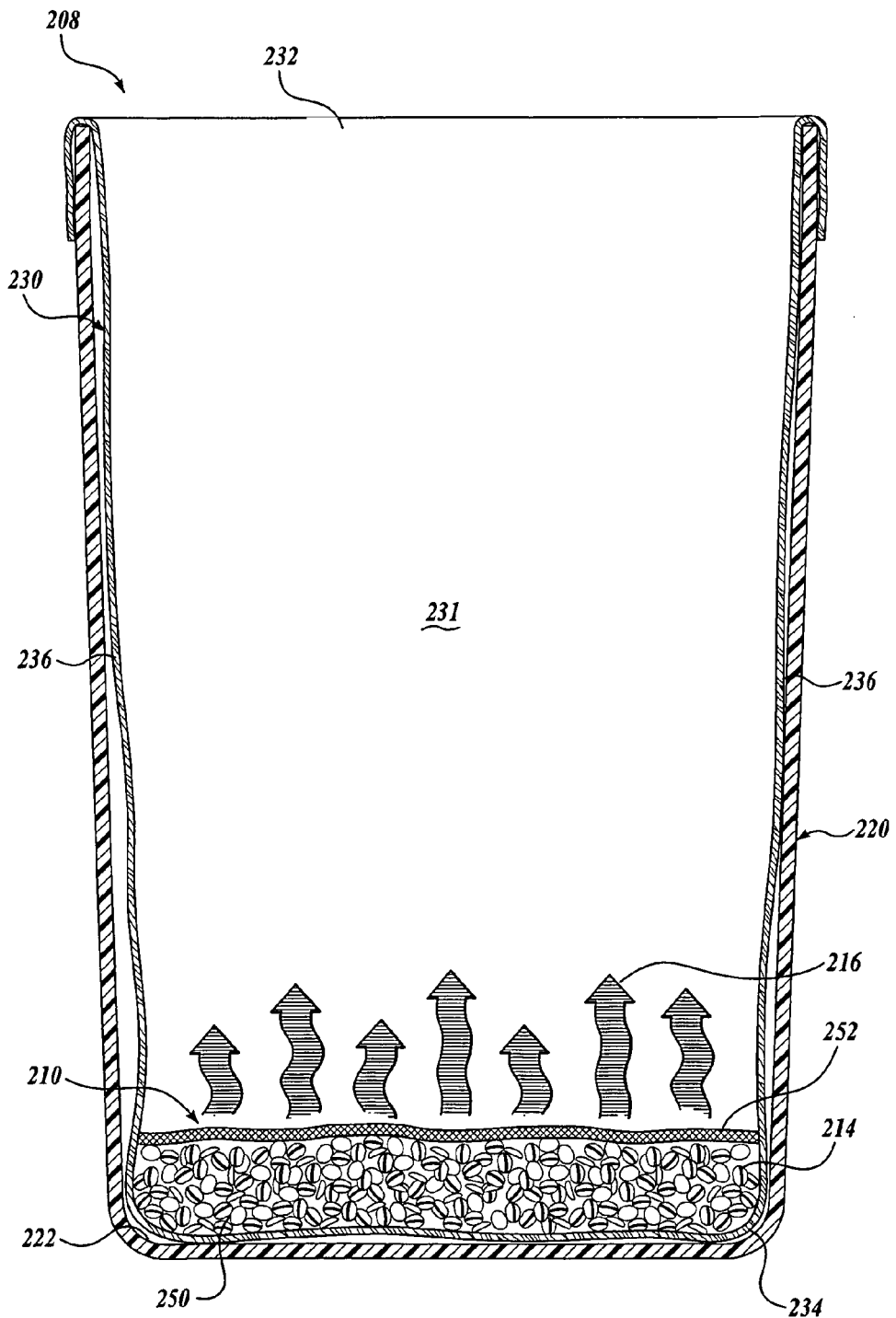
FIG. 4 is a cross-sectional view of an alternate embodiment of the deodorizer assembly in accordance with the present disclosure.

Referring to FIG. 4, a second alternate embodiment of a deodorizer assembly 208 shown in use with a garbage container 220 is depicted. The deodorizer assembly 208 is comprised of a disposable liner 230 having an interior portion 231, an open end 232, an opposing closed end 234, and sides 236 connecting the open end 232 with the closed end 234. As seen in FIG. 4, the liner 230 is configured to fit within a suitable garbage container 220, similar to a garbage bag. For example, the liner 230 may be U-shaped in cross-section. However, other configurations of the liner 230 are possible, and the liner 230 may be configured to fit inside any suitable garbage container 220, including but not limited to containers designed for interior household use, curbside cans, recycling cans, dumpsters, and equivalents thereof. The liner 230 is preferably made from a compostable or biodegradable material.

Referring still to FIG. 4, the deodorizer assembly 208 further comprises a deodorizer 210 disposed within the interior portion 231 of the liner 230. The deodorizer 210 is defined by a crushable compostable material 214 contained within a compartment 250 located within the interior portion 231 of the liner 230, preferably within the closed end 234 of the liner 230. The compartment 250 is defined by a piece of enclosing material 252 that extends between the sides 236 of the liner 230 to enclose the bottom interior portion of the liner 230. The enclosing material 252 is sufficiently porous to allow the deodorant aroma 216 produced by the crushable compostable material 214 to diffuse from the interior of the compartment 250 to the interior portion 231 of the liner 230. In addition, the enclosing material 252 may be permeable to gas flow, such as a deodorant aroma 216, but impermeable to liquids.

A preferred crushable compostable material 214 is coffee beans. Some of the coffee beans may be precrushed to release the deodorant aroma 216 of coffee before adding garbage to the container. In other embodiments, the deodorizer assembly 208 may comprise another natural or artificial compostable material that releases a deodorant when crushed, such as charcoal. In the alternative, the crushable material may be a container filled with a solid or liquid deodorant that releases the deodorant when crushed.

Referring to FIG. 4, the manner in which the deodorizer assembly 208 is used will be hereinafter described. The liner 230 is inserted within a garbage container 220 with the closed end 234 disposed at the interior bottom portion 222 of the garbage container 220. The liner 230 may be secured within the garbage container 220 in a manner well known in the art, such as by stretching a top portion of the sides 236 over the top edge of the garbage container 220. With the liner 230 secured within the garbage container 220, the liner 230 may be seen as an attachment assembly for securing the deodorizer 210 within the garbage container 220.

The crushable compostable material 214 is crushed by the weight of the garbage that is added to the interior portion 231 of the liner 230. As the compostable material 214 is crushed by the weight of the garbage, the crushable compostable material 214 releases a deodorant aroma 216 that passes from the interior of the compartment 250 to the interior portion 231 of the liner 230. When the garbage is ready to be emptied, the deodorizer liner 230 containing the garbage is removed, and a new deodorizer assembly 208 is inserted within the garbage container 220. The used deodorizer assembly 208 containing garbage may then be disposed of, preferably by composting.

Although the subject matter has been described in language specific to structural features, it is to be understood that the subject matter defined in the appended claims is not necessarily limited to the specific features described above. Rather, the specific features described above are disclosed as example forms of implementing the claims. While illustrative embodiments have been illustrated and described, it will be appreciated that various changes can be made therein without departing from the spirit and scope of the disclosure.

The embodiments of the present disclosure in which an exclusive property or privilege is claimed are defined as follows:

1. A deodorizer assembly, comprising:
   (a) a garbage container defined by an interior portion, an open end, and a closed end that opposes the open end and is connected to the open end by a side portion having a length;
   (b) a deodorizer comprising a crushable compostable material disposed within a compartment defined at least in part by a compostable material that is substantially porous to allow gas flow from an interior portion of the compartment to an exterior portion, the deodorizer sized and configured to be positioned against a bottom interior surface of the garbage container defined at the closed end of the garbage container; and
   (c) an attachment assembly defined within the interior portion of the garbage container, the attachment assembly configured to removably secure the deodorizer to the interior portion of the garbage container, the attachment assembly comprising:
      (i) at least one channel-defining structure formed on or otherwise secured to an interior surface of the side portion of the garbage container, defining a length, and including a open top end and an open bottom end and extending along at least a portion of the length of the side portion of the garbage container in a vertical direction to define at least one permanent channel extending along the length of the side portion of the garbage container; and (ii) at least one elongated member slidably and removably disposed within the at least one channel-defining structure and having a length greater than the length of said channel-defining structure, wherein the elongated member is engageable with the deodorizer to releasably secure the deodorizer against the bottom interior surface of the garbage container and securably retains the deodorizer when the garbage container is inverted.

2. The deodorizer assembly of claim 1, wherein the crushable compostable material comprises coffee beans.

3. The deodorizer assembly of claim 1, wherein at least some of the crushable compostable material is crushable by the weight of garbage added to the garbage container.

4. A deodorizer assembly, comprising:

(a) a garbage container defined by an interior portion, an open end, and a closed end that opposes the open end and is connected to the open end by a side portion having a length;

(b) a deodorizer comprising a crushable deodorizing material disposed within a compartment that is substantially porous to allow gas flow from an interior portion of the compartment to an exterior portion, the deodorizer sized and configured to be positioned against a bottom interior surface of the garbage container defined at the closed end of the garbage container; and (c) an attachment assembly defined within the interior portion of the garbage container, the attachment assembly configured to removably secure the deodorizer to the interior portion of the garbage container~the attachment assembly comprising:

(i) at least one channel-defining structure formed on or otherwise secured to an interior surface of the side portion of the garbage container, defining a length, and including a open top end and an open bottom end and extending along at least a portion of the length of the side portion of the garbage container in a vertical direction to define at least one permanent channel extending along the length of the side portion of the garbage container; and (ii) at least one elongated member slidably and removably disposed within the at least one channel-defining structure and having a length greater than the length of said channel-defining structure, wherein the elongated member is engageable with the deodorizer to releasably secure the deodorizer against the bottom interior surface of the garbage container and securably retains the deodorizer when the garbage container is inverted.

5. The deodorizer assembly of claim 4, wherein the crushable deodorizing material comprises coffee beans.

6. The deodorizer assembly of claim 4, wherein at least some of the crushable deodorizing material is crushable by the weight of garbage added to the garbage container.

* * * * *